(12) United States Patent
Choo et al.

(10) Patent No.: US 9,980,954 B2
(45) Date of Patent: May 29, 2018

(54) QUINOLINE DERIVATIVES FOR INHIBITING HISTONE METHYLTRANSFERASES AND USE THEREOF

(71) Applicant: KOREA INSTITUTE OF SCIENCE AND TECHNOLOGY, Seoul (KR)

(72) Inventors: Hyunah Choo, Seoul (KR); Sun-Joon Min, Seoul (KR); Yun Kyung Kim, Seoul (KR); Hoon Ryu, Seoul (KR); Hyemyung Seo, Yongin-si (KR); Juhyeon Kim, Seoul (KR); Jihoon Jang, Ansan-si (KR); Sungsu Lim, Seoul (KR); Younghee Kim, Suwon-si (KR); Yu Jin Hwang, Seoul (KR); Yong Seo Cho, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days. days.

(21) Appl. No.: 15/403,404

(22) Filed: Jan. 11, 2017

(65) Prior Publication Data

US 2017/0354650 A1      Dec. 14, 2017

(51) Int. Cl.
*A61K 31/47* (2006.01)
*A61K 31/4709* (2006.01)
*A61K 31/5377* (2006.01)

(52) U.S. Cl.
CPC .......... *A61K 31/47* (2013.01); *A61K 31/4709* (2013.01); *A61K 31/5377* (2013.01)

(58) Field of Classification Search
CPC .......................... A61K 31/47; A61K 31/4709
See application file for complete search history.

(56) References Cited

U.S. PATENT DOCUMENTS

| 7,989,628 B2 * | 8/2011 | Kolczewski | C07D 215/38 546/159 |
| 8,642,660 B2 * | 2/2014 | Goldfarb | A61K 31/122 514/18.9 |

OTHER PUBLICATIONS

Bennett et al (1949): STN International, HCAPLUS database (Columbus, Ohio), Accession No. 1949: 50529.*
Lack et al (2011): STN International, HCAPLUS database (Columbus, Ohio), Accession No. 2011: 1692287.*
Sharma et al (2015): STN International, HCAPLUS database (Columbus, Ohio), Accession No. 2015: 403929.*
Nicholas A. Di Prospero et al., Therapeutics Development for Triplet Repeat Expansion Diseases, Nature Reviews | Genetics, Oct. 2005, pp. 756-765, vol. 6, Nature Publishing Group.
Ryu et al., ESET/SETDB1 gene expression and histone H3 (K9) trimethylation in Huntington's disease, Dec. 12, 2006, pp. 19176-19181, vol. 103, No. 50, PNAS.

* cited by examiner

*Primary Examiner* — Golam M Shameem
(74) *Attorney, Agent, or Firm* — Golodilocks Zone IP Law (57) ABSTRACT

The present disclosure relates to a quinoline derivative which inhibits the activity of histone methyltransferases (ESET/SETDB1) specific for the histone molecule H3K9 or a pharmaceutically acceptable salt thereof and a use thereof.

6 Claims, 4 Drawing Sheets

QUINOLINE DERIVATIVES FOR INHIBITING HISTONE METHYLTRANSFERASES AND USE THEREOF

CROSS-REFERENCE TO RELATED APPLICATIONS

This application claims, under 35 U.S.C. § 119, the priority of Korean Patent Application No. 10-2016-0071219 filed on Jun. 8, 2016 in the Korean Intellectual Property Office, the disclosure of which is incorporated herein by reference in its entirety.

TECHNICAL FIELD

The present disclosure relates to a quinoline derivative which inhibits the activity of histone methyltransferases (ESET/SETDB1) specific for the histone molecule H3K9 or a pharmaceutically acceptable salt thereof and a use thereof.

BACKGROUND

Huntington's disease is the third most common degenerative brain disease after Alzheimer's disease and Parkinson's disease. It is a rare intractable inherited disease characterized by disorder in motion and cognition due to the degeneration of brain cells. The cause of Huntington's disease is the mutation of the Huntingtin gene located on chromosome 4 due to abnormally increased CAG repeat sequences. It is known that this mutation causes Huntington's disease by resulting in death of nerve cells [Di Prospero and Fischbeck; *Nature Reviews Genetics* (2005) 6:756-765].

Normal people have 35 or less CAG repeats. If the number of the CAG repeats is 36 or larger, there is a risk of Huntington's disease. And, if it is 40 or larger, there is a high risk of Huntington's disease. It is known that the disease occurs at younger ages as the number of the CAG repeats is larger. 60 or more CAG repeats were found in patients who were diagnosed with Huntington's disease in adolescence.

Xenazine (tetrabenazine) is the representative drug used for patients with Huntington's disease. However, Xenazine merely reduces movement disorder by decreasing the level of dopamine in the body and cannot fundamentally treat the chromosome anomaly which is the cause of Huntington's disease. It was reported that increased trimethylation at histone H3 lysine 9 (H3K9) was observed in the brain tissue of a patient who died of Huntington's disease and that ESET (a.k.a. SETDB1) is the important enzyme that trimethylates H3K9. ESET stands for ERG-associated protein with SET domain, where ERG means erythroblast transformation specific-related gene (ETS-related gene), and SETDB1 stands for SET domain bifurcated 1 (hereinafter, referred to as 'ESET/SETDB1'). ESET/SETDB1 was reported as a molecular target for treatment of Huntington's disease because increased R6 mouse survival time was found in the R6 model which is an animal model of Huntington's disease when the expression of ESET/SETDB1 was inhibited (*PNAS*, 2006, 103, 19176-19181). At present, no compound is known as an ESET/SETDB1 inhibitor and there is a need for development of an ESET/SETDB1 inhibitor for treatment of Huntington's disease.

SUMMARY

The present disclosure is directed to providing a quinoline derivative which inhibits histone methyltransferase that specifically acts on histone H3 lysine 9 or a pharmaceutically acceptable salt thereof.

The present disclosure is also directed to providing a composition for treating or preventing Huntington's disease which contains the quinoline derivative for inhibiting histone methyltransferase or a pharmaceutically acceptable salt thereof as an active ingredient.

In an aspect, the present disclosure provides a quinoline derivative represented by [Chemical Formula 1] or a pharmaceutically acceptable salt thereof, which inhibits histone methyltransferase (H3K9 methyltransferase), and a method for preparing the same:

[Chemical Formula 1]

wherein
Z is O or NH,
each of $R_1$ and $R_2$, which are identical to or different from each other, is independently selected from H, $C_{1-6}$ alkyl, hydroxy $C_{1-6}$ alkyl, phenyl and $C_{4-7}$ cycloalkyl, wherein the phenyl is unsubstituted or substituted with a substituent selected from OH, $NO_2$, a halogen, $C_{1-3}$ alkyl, $C_{1-3}$ alkoxy and trifluoromethyl, the $R_2$ is $C_{4-7}$ cycloalkyl if the $R_1$ is H, the $R_1$ is $C_{4-7}$ cycloalkyl if the $R_2$ is H, and the $R_1$ and the $R_2$ may be linked with each other to form a ring if they are $C_{1-6}$ alkyl or hydroxy $C_{1-6}$ alkyl, and
$R_3$ is selected from H, $C_{1-10}$ alkyl, vinyl, allyl $C_{0-6}$ alkyl and propargyl $C_{0-6}$ alkyl.

In another aspect, the present disclosure provides a pharmaceutical composition for treating or preventing Huntington's disease, which contains the quinoline derivative represented by [Chemical Formula 1] or the pharmaceutically acceptable salt thereof as an active ingredient.

The quinoline derivative represented by [Chemical Formula 1] or the pharmaceutically acceptable salt thereof according to the present disclosure can prevent or treat Huntington's disease by effectively inhibiting the activity of histone methyltransferase (H3K9 methyltransferase) and thereby preventing trimethylation of histone H3 lysine 9.

The quinoline derivative or the pharmaceutically acceptable salt thereof according to the present disclosure can inhibit trimethylation of histone H3 lysine 9 by inhibiting the activity of the histone methyltransferase ESET/SETDB1 which specifically acts on histone H3 lysine 9 (H3K9). Accordingly, the composition which contains the quinoline derivative or the pharmaceutically acceptable salt thereof according to the present disclosure as an active ingredient can be used as an agent for treating or preventing a disease related with trimethylation of H3K9, specifically Huntington's disease.

DETAILED DESCRIPTION OF EMBODIMENTS

Hereinafter, the present disclosure is described in more detail.

In an aspect, the present disclosure provides a quinoline derivative represented by [Chemical Formula 1] or a pharmaceutically acceptable salt thereof, which inhibits histone methyltransferase (H3K9 methyltransferase):

[Chemical Formula 1]

wherein
Z is O or NH,
each of $R_1$ and $R_2$, which are identical to or different from each other, is independently selected from H, $C_{1-6}$ alkyl, hydroxy $C_{1-6}$ alkyl, phenyl and $C_{4-7}$ cycloalkyl, wherein the phenyl is unsubstituted or substituted with a substituent selected from OH, $NO_2$, a halogen, $C_{1-3}$ alkyl, $C_{1-3}$ alkoxy and trifluoromethyl, the $R_2$ is $C_{4-7}$ cycloalkyl if the $R_1$ is H, the $R_1$ is $C_{4-7}$ cycloalkyl if the $R_2$ is H, and the $R_1$ and the $R_2$ may be linked with each other to form a ring if they are $C_{1-6}$ alkyl or hydroxy $C_{1-6}$ alkyl, and
$R_3$ is selected from H, $C_{1-10}$ alkyl, vinyl, allyl $C_{0-6}$ alkyl and propargyl $C_{0-6}$ alkyl.

In the present disclosure, the ring formed as the $R_1$ and the $R_2$ are linked with each other may be morpholino or cycloalkyl, and the cycloalkyl may be specifically $C_{4-7}$ cycloalkyl, more specifically $C_{5-6}$ cycloalkyl.

In the present disclosure, the allyl $C_{0-6}$ alkyl and propargyl $C_{0-6}$ alkyl may be allyl and propargyl, respectively, where each number of carbon atoms is zero.

In the present disclosure, "alkyl" refers to a straight (linear) or branched saturated hydrocarbon group having the specified number of carbon atoms.

In the present disclosure, histone methyltransferase may be ESET (erythroblast transformation specific-related gene associated protein with SET domain) or SETDB1 (SET domain, bifurcated 1) which induces methylation of histone H3 lysine 9.

In the present disclosure, the pharmaceutically acceptable salt is not specially limited as long as it is one commonly used in the related art. As a specific example, the salt may be formed using a nontoxic inorganic acid such as hydrochloric acid, bromic acid, sulfonic acid, amidosulfuric acid, phosphoric acid and nitric acid or a nontoxic organic acid such as acetic acid, propionic acid, succinic acid, glycolic acid, stearic acid, lactic acid, tartaric acid, citric acid, p-toluenesulfonic acid and methanesulfonic acid.

In the present disclosure, the quinoline compound represented by [Chemical Formula 1] may be selected from the compounds represented by [Chemical Formula 2] through [Chemical Formula 4].

[Chemical Formula 2]

[Chemical Formula 3]

[Chemical Formula 4]

In [Chemical Formula 2] through [Chemical Formula 4],
Z is O or NH,
Y is C or O,
$R_3$ is selected from H, $C_{1-10}$ alkyl, vinyl, allyl $C_{0-6}$ alkyl and propargyl $C_{0-6}$ alkyl,
$R_4$ is selected from H, OH, $NO_2$, a halogen, $C_{1-3}$ alkyl, $C_{1-3}$ alkoxy and trifluoromethyl, and
each of n and m, which are identical to or different from each other, is independently an integer from 1 to 5.

In the present disclosure, particularly preferred examples of the quinoline compound represented by [Chemical Formula 1] may be Compound 1 through Compound 17 or pharmaceutically acceptable salts thereof.

Compound 1: $N^2$-cyclopentyl-$N^5$-allylquinoline-2,5-diamine;
Compound 2: $N^2$-cyclohexyl-$N^5$-allylquinoline-2,5-diamine;
Compound 3: 2-(pyrrolidin-1-yl)-N-allylquinolin-5-amine;
Compound 4: 2-(piperidin-1-yl)-N-allylquinolin-5-amine;
Compound 5: $N^2$-phenyl-$N^5$-allylquinoline-2,5-diamine;
Compound 6: 2-morpholino-N-allylquinolin-5-amine;
Compound 7: 5-allyloxy-N-cyclopentylquinolin-2-amine;
Compound 8: 5-allyloxy-2-(pyrrolidin-1-yl)quinoline;
Compound 9: 5-allyloxy-2-(piperidin-1-yl)quinoline;
Compound 10: 4-(5-allyloxyquinolin-2-yl)morpholine;
Compound 11: 5-allyloxy-N-phenylquinolin-2-amine;
Compound 12: 2-cyclopentylaminoquinolin-5-ol;
Compound 13: 2-(pyrrolidin-1-yl)quinolin-5-ol;
Compound 14: 2-(piperidin-1-yl)quinolin-5-ol;

Compound 15: 2-(phenylamino)quinolin-5-ol;
Compound 16: 2-morpholinoquinolin-5-ol;
Compound 17: 5-propargyloxy-2-(pyrrolidin-1-yl)quinoline.

The present disclosure also provides a method for preparing the quinoline derivative represented by [Chemical Formula 1]. The quinoline derivative represented by [Chemical Formula 1] according to the present disclosure may be prepared by two methods. The preparation method differs depending on the heteroatom of the Z in [Chemical Formula 1].

First, if the Z is NH, the quinoline derivative represented by [Chemical Formula 1] may be prepared by reacting zinc(I) iodide, tripotassium phosphate and ethylene glycol in an organic solvent and activating by adding $ZR_3H$; and performing reaction by adding a compound represented by [Chemical Formula 5]:

[Chemical Formula 5]

[Chemical Formula 1]

In [Chemical Formula 1] and [Chemical Formula 5], Z, X, $R_1$, $R_2$ and $R_3$ are the same as defined above.

In the present disclosure, the organic solvent may be selected from a group consisting of a $C_{1-4}$ alcohol, acetonitrile, dichloromethane, dichloroethane, tetrahydrofuran, ethyl acetate, dioxane, N,N-dimethylformamide and dimethyl sulfoxide. Specifically, it may be isopropyl alcohol.

The reaction may be performed by refluxing at 60-100° C. for 6-36 hours.

In an exemplary embodiment of the present disclosure, the reaction product may be extracted using an organic solvent commonly used for extraction. Specifically, the reaction product may be diluted in an organic solvent selected from dichloromethane, diethyl ether and ethyl acetate and then purified by removing water remaining in the organic layer and then concentrating.

The purification may be performed by a commonly used method. Specifically, the quinoline derivative represented by [Chemical Formula 1] may be obtained as the target compound by purifying by column chromatography using silica gel.

The quinoline derivative represented by [Chemical Formula 1] may be prepared in the form of a pharmaceutically acceptable salt using a nontoxic inorganic acid such as hydrochloric acid, bromic acid, sulfonic acid, amidosulfuric acid, phosphoric acid and nitric acid or a nontoxic organic acid such as acetic acid, propionic acid, succinic acid, glycolic acid, stearic acid, lactic acid, tartaric acid, citric acid, p-toluenesulfonic acid and methanesulfonic acid.

In an exemplary embodiment of the present disclosure, the compound represented by [Chemical Formula 5] may be prepared by: synthesizing a compound represented by [Chemical Formula 7] by introducing a halogen substituent to a compound represented by [Chemical Formula 6]; and reacting the compound represented by [Chemical Formula 7] with $NR_1R_2H$:

[Chemical Formula 6]

[Chemical Formula 7]

In [Chemical Formula 6] and [Chemical Formula 7], Z, $R_1$, $R_2$ and $R_3$ are the same as defined above, and each of X and X', which are identical to or different from each other, is independently a halogen selected from chloro, bromo and iodo.

In the present disclosure, the compound represented by [Chemical Formula 6] may be prepared by substituting the amine group of 5-aminoquinoline with a halogen (X). As a specific example, it may be prepared by cooling 5-aminoquinoline to low temperature, adding a strong acid such as HCl and stirring the mixture, performing reaction by adding a sodium nitrate solution, and then performing reaction by adding HI in the presence of copper(I) iodide.

In the present disclosure, the compound represented by [Chemical Formula 7] may be prepared by reacting the compound represented by [Chemical Formula 6] with mCPBA (m-chloroperoxybenzoic acid) in an organic solvent to prepare an N-oxide, and then reacting with $POCl_3$.

Next, if the Z is O, the quinoline derivative represented by [Chemical Formula 1] may be prepared by preparing a compound represented by [Chemical Formula 8] by reacting 5-hydroxyquinoline with $R_3'Br$; synthesizing a compound represented by [Chemical Formula 9] by introducing a halogen substituent to the compound represented by [Chemical Formula 8]; and heating the compound represented by [Chemical Formula 9] and $NR_1R_2H$ under reflux.

[Chemical Formula 8]

[Chemical Formula 9]

In [Chemical Formula 1], [Chemical Formula 8] and [Chemical Formula 9], Z is O, X is a halogen, and $R_3'$ is selected from $C_{1-10}$ alkyl, vinyl, allyl $C_{0-6}$ alkyl and propargyl $C_{0-6}$ alkyl.

In the present disclosure, a compound wherein the $R_3$ in [Chemical Formula 1] is H may be prepared by a method which further includes heating the compound represented by [Chemical Formula 9] and $NR_1R_2H$ under reflux and removing the $R_3$ by stirring in the presence of $Pd(PPh_3)_4$ and $K_2CO_3$ under nitrogen flow.

In another aspect, the present disclosure provides a pharmaceutical composition for treating or preventing Huntington's disease, which contains the quinoline derivative represented by [Chemical Formula 1] or the pharmaceutically acceptable salt thereof as an active ingredient.

The quinoline derivative represented by [Chemical Formula 1] or the pharmaceutically acceptable salt thereof according to the present disclosure can prevent or treat Huntington's disease by inhibiting the activity of histone methyltransferase (H3K9 methyltransferase) and thereby preventing trimethylation of histone H3 lysine 9.

In an exemplary embodiment of the present disclosure, the quinoline derivative or the pharmaceutically acceptable salt thereof may be prepared into a form suitable for oral or parenteral administration by a common formulation method by mixing with a commonly used carrier, adjuvant or diluent.

The carrier, adjuvant or diluent may be lactose, dextrose, sucrose, sorbitol, mannitol, xylitol, erythritol, maltitol, starch, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate or mineral oil.

When formulating, a common filler, extender, binder, humectant, disintegrant, surfactant, etc. may be further included and a lubricant such as magnesium stearate and talc may be further added.

For oral administration, the quinoline derivative or the pharmaceutically acceptable salt thereof may be prepared into a tablet, a capsule, a solution, a syrup, a suspension, etc., and, for parenteral administration, it may be prepared into an injection for intraabdominal, subcutaneous, intramuscular or transdermal administration.

In an exemplary embodiment of the present disclosure, the pharmaceutical composition as an agent which acts on histone methyltransferase may contain the quinoline derivative of [Chemical Formula 1] or the pharmaceutically acceptable salt thereof at an effective daily dosage of 0.01-1000 mg/day for an adult. However, the administration dosage may vary depending on the age, body weight and sex of the patient, administration type, health condition and severity of disease. The dosage may be administered once or several times a day depending on the discretion of a physician or a pharmacist.

The present disclosure also provides a medical use of the pharmaceutical composition containing the quinoline derivative of [Chemical Formula 1] or the pharmaceutically acceptable salt thereof for prevention or treatment of a disease.

That is to say, the present disclosure provides a medical use for prevention or treatment of Huntington's disease by inhibiting the activity of histone methyltransferase (H3K9 methyltransferase) and thereby preventing trimethylation of histone H3 lysine 9.

Hereinafter, the present disclosure will be described in more detail through examples. However, it will be obvious to those of ordinary skill in the art that the following examples are for illustrative purposes only and not intended to limit the scope of this disclosure.

EXAMPLES

Example 1

Example 1.1: Preparation of 5-iodoquinoline

After adding 5-aminoquinoline (333 mg, 2.31 mmol) to a flask and cooling to 0° C., 1.6 N HCl (7.70 mL) was slowly added. To the solution which turned red, an aqueous solution (4.00 mL) of sodium nitrite (530 mg, 7.68 mmol) was slowly added at 0° C. 10 minutes later, to the solution which turned brown, an aqueous solution (6.70 mL) of copper(I) iodide (530 mg, 2.78 mmol) was slowly added at 0° C. $N_2$ gas was produced and the copper(I) iodide was added after completely dispersing in $H_2O$ as a solvent. Then, 57% HI (3.35 mL) was slowly added at 0° C. 10 minutes later, the reaction mixture was stirred at 60° C. for 3 hours. After cooling the reaction mixture to room temperature and adding ice, 4 N NaOH was slowly added until the pH reached 14. The reaction mixture was separated into an ethyl acetate layer and an $H_2O$ layer using a separatory funnel. After drying the organic layer with anhydrous $MgSO_4$, the solvent was removed by vacuum distillation. The mixture was purified by silica gel column chromatography (ethyl acetate:hexane=1:1) to obtain the target compound (yellow solid, 422 mg, 72%).

$^1H$ NMR (CDCl$_3$, 400 MHz) δ 8.89 (dd, $J_1$=4.2 Hz, $J_2$=1.5 Hz, 1H), 8.39 (d, J=8.5 Hz, 1H), 8.13 (d, J=6.5 Hz, 1H), 8.11 (d, J=8.3 Hz, 1H), 7.49 (dd, $J_1$=9.6 Hz, $J_2$=3.2 Hz, 1H), 7.44 (t, J=7.9 Hz, 1H).

Example 1.2: Preparation of 2-chloro-5-iodoquinoline

After dissolving 5-iodoquinoline (709 mg, 2.78 mmol) in dichloromethane (14.0 mL) and adding mCPBA (1.26 g, 4.16 mmol) at 0° C., the mixture was stirred at room temperature for 4 hours. After confirming the formation of N-oxide by TLC (ethyl acetate:hexane=1:1, $R_f$=0.1), 4 N NaOH was slowly added until the pH reached 10. The reaction mixture was separated into a dichloromethane layer and an $H_2O$ layer using a separatory funnel. After drying the organic layer with anhydrous $MgSO_4$, the solvent was removed by vacuum distillation. After dissolving the dried N-oxide mixture in dichloromethane (11.0 mL), POCl$_3$ (0.40 mL, 4.29 mmol) was slowly added. The reaction mixture was stirred at 60° C. for 2 hours. After confirming the termination of reaction by TLC (ethyl acetate:hexane=1:4, $R_f$=0.8), the reaction mixture was slowly dropped into a flask set to 0° C. using ice and water and 4 N NaOH was slowly added until the pH reached 10. The reaction mixture was separated into a dichloromethane layer and an $H_2O$ layer using a separatory funnel. After drying the organic layer with anhydrous $MgSO_4$, the solvent was removed by vacuum distillation. The mixture was purified by silica gel column chromatography (dichloromethane:hexane=2:1) to obtain the target compound (yellow solid, 383 mg, 48%).

$^1H$ NMR (CDCl$_3$, 300 MHz) δ 8.39 (dd, $J_1$=8.7 Hz, $J_2$=0.6 Hz, 1H), 8.16 (dd, $J_1$=7.5 Hz, $J_2$=1.2 Hz, 1H), 8.06 (d, J=8.4 Hz, 1H), 7.48 (d, J=8.7 Hz, 1H).

Example 1.3: Preparation of N-cyclopentyl-5-iodoquinolin-2-amine

After adding 2-chloro-5-iodoquinoline (3, yellow solid, 25 mg, 86.4 µmol) to a vial and dissolving in ethanol (0.86 mL), TEA (0.06 mL, 0.43 mmol) was added and cyclopentylamine (13 μL, 0.13 mmol) was slowly added. The reaction mixture was stirred at 140° C. for 9 hours. After confirming the termination of reaction by TLC (ethyl acetate:hexane=1:4, $R_f$=0.7), excess TEA and ethanol were removed by vacuum distillation. The reaction mixture was separated into an ethyl acetate layer and an H$_2$O layer using a separatory funnel. After drying the organic layer with anhydrous MgSO$_4$, the solvent was removed by vacuum distillation. The mixture was purified by silica gel column chromatography (ethyl acetate:hexane=1:4) to obtain the target compound (yellow oil, 29 mg, 99%).

$^1$H NMR (CDCl$_3$, 300 MHz) δ 8.07 (d, J=9.0 Hz, 1H), 7.77 (dd, J$_1$=7.2 Hz, J$_2$=0.9 Hz, 1H), 7.65 (d, J=8.4 Hz, 1H), 7.24 (t, J=7.9 Hz, 1H), 6.72 (d, J=9.3 Hz, 1H), 4.96 (bs, 1H), 4.32 (m, 1H), 2.16 (m, 2H), 1.74 (m, 4H), 1.56 (m, 2H).

Example 1.4: Preparation of N$^2$-cyclopentyl-N$^5$-allylquinoline-2,5-diamine (Compound 1)

Copper(I) iodide (1.19 mg, 6.25 μmol) and tripotassium phosphate (50.0 mg, 0.236 mmol) were stirred in a vial. After adding isopropyl alcohol (125 μL) and adding ethylene glycol (14.0 μmL, 0.251 mmol), the resulting azure reaction mixture was stirred. 10 minutes later, after adding allyl amine (11.0 μmL, 0.147 mmol), the resulting blue reaction mixture was stirred. Then, N-cyclopentyl-5-iodo-quinolin-2-amine (yellow oil, 42 mg, 0.124 mmol) dissolved in isopropyl alcohol (125 μL) was slowly added. The reaction mixture was stirred at 80° C. for 24 hours. After confirming the termination of reaction by TLC (ethyl acetate:hexane=1:1, $R_f$=0.7), H$_2$O was added to the reaction mixture. The reaction mixture was separated into an ethyl acetate layer and an H$_2$O layer using a separatory funnel. After drying the organic layer with anhydrous MgSO$_4$, the solvent was removed by vacuum distillation. The mixture was purified by silica gel column chromatography (ethyl acetate:hexane=1:1) to obtain the target compound (yellow oil, 24 mg, 72%).

$^1$H NMR (CDCl$_3$, 400 MHz) 7.89 (d, J=9.1 Hz, 1H), 7.37 (t, J=8.1 Hz, 1H), 7.06 (d, J=8.4 Hz, 1H), 6.60 (d, J=9.2 Hz, 1H), 6.38 (d, J=7.7 Hz, 1H), 6.10-6.01 (m, 1H), 5.35 (dd, J$_1$=17.2 Hz, J$_2$=1.5 Hz, 1H), 5.22 (dd, J$_1$=10.3 Hz, J$_2$=1.4 Hz, 1H), 4.89 (bs, 1H), 4.24 (bs, 1H), 4.24-4.18 (m, 1H), 3.89 (d, J=4.3 Hz, 2H), 2.11-2.05 (m, 2H), 1.78-1.70 (m, 2H), 1.67-1.63 (m, 2H), 1.54-1.48 (m, 2H).

Example 2: Preparation of N$^2$-cyclohexyl-N$^5$-allylquinoline-2,5-diamine (Compound 2)

Compound 2 having a cyclohexyl substituent was obtained in the same manner as in Examples 1.3 and 1.4.

$^1$H NMR (CDCl$_3$, 400 MHz) 7.89 (d, J=9.2 Hz, 1H), 7.39 (t, J=8.1 Hz, 1H), 7.08 (d, J=8.4 Hz, 1H), 6.58 (d, J=9.2 Hz, 1H), 6.39 (d, J=7.7 Hz, 1H), 6.11-6.02 (m, 1H), 5.36 (dd, J=17.2 Hz, J=1.5 Hz, 1H), 5.24 (dd, J$_1$=10.3 Hz, J$_2$=1.3 Hz, 1H), 4.74 (d, J=4.9 Hz, 1H), 4.26 (bs, 1H), 3.91 (s, 2H), 3.82-3.75 (m, 1H), 2.13-2.07 (m, 2H), 1.82-1.77 (m, 2H), 1.70-1.66 (m, 1H), 1.51-1.40 (m, 2H), 1.30-1.21 (m, 3H).

Example 3: Preparation of 2-(pyrrolidin-1-yl)-N-allylquinolin-5-amine (Compound 3)

Compound 3 having a pyrrolidine substituent was obtained in the same manner as in Examples 1.3 and 1.4.

$^1$H NMR (CDCl$_3$, 300 MHz) δ 7.93 (d, J=9.3 Hz, 1H), 7.41 (t, J=7.5 Hz, 1H), 7.17 (d, J=8.4 Hz, 1H), 6.67 (d, J=9.3 Hz, 1H), 6.40 (d, J=7.8 Hz, 1H), 6.16-6.05 (m, 1H), 5.39 (dd, J$_1$=17.1 Hz, J$_2$=1.2 Hz, 1H), 5.26 (d, J=10.2 Hz, 1H), 3.94 (d, J=5.4 Hz, 2H), 3.67-3.63 (m, 4H), 2.09-2.05 (m, 4H).

Example 4: Preparation of 2-(piperidin-1-yl)-N-allylquinolin-5-amine (Compound 4)

Compound 4 having a piperidine substituent was obtained in the same manner as in Examples 1.3 and 1.4.

$^1$H NMR (CDCl$_3$, 300 MHz) δ 7.93 (d, J=9.3 Hz, 1H), 7.41 (t, J=8.1 Hz, 1H), 7.16 (d, J=8.4 Hz, 1H), 6.93 (d, J=9.3 Hz, 1H), 6.42 (d, J=7.8 Hz, 1H), 6.15-6.04 (m, 1H), 5.39 (dd, J$_1$=17.1 Hz, J$_2$=1.5 Hz, 1H), 5.26 (dd, J$_1$=10.2 Hz, J$_2$=1.5 Hz, 1H), 4.26 (s, 1H), 3.94 (d, J=4.8 Hz, 2H), 3.74 (bs, 4H), 1.72 (bs, 6H).

Example 5: Preparation of N$^2$-Phenyl-N$^5$-allylquinoline-2,5-diamine (Compound 5)

Compound 5 having a phenylamine substituent was obtained in the same manner as in Examples 1.3 and 1.4.

$^1$H NMR (CDCl$_3$, 300 MHz) δ 7.97 (d, J=9.1 Hz, 1H), 7.52 (dd, J$_1$=8.5 Hz, J$_2$=1.0 Hz, 2H), 7.45 (t, J=8.1 Hz, 1H), 7.36 (t, J=7.9 Hz, 2H), 7.20 (d, J=8.4 Hz, 1H), 7.08 (t, J=7.4 Hz, 1H), 6.94 (d, J=9.1 Hz, 1H), 6.82 (s, 1H), 6.47 (d, J=7.7 Hz, 1H), 6.13-6.00 (m, 1H), 5.36 (dd, J$_1$=17.2 Hz, J$_2$=1.5 Hz, 1H), 5.24 (dd, J$_1$=10.3 Hz, J$_2$=1.4 Hz, 1H), 4.29 (s, 1H), 3.91 (s, 2H).

Example 6: Preparation of 2-morpholino-N-allylquinolin-5-amine (Compound 6)

Compound 6 having a morpholino substituent was obtained in the same manner as in Examples 1.3 and 1.4.

$^1$H NMR (CDCl$_3$, 300 MHz) δ 7.96 (d, J=9.3 Hz, 1H), 7.40 (t, J=8.0 Hz, 1H), 7.14 (d, J=8.4 Hz, 1H), 6.86 (d, J=9.3 Hz, 1H), 6.42 (d, J=7.8 Hz, 1H), 6.11-6.00 (m, 1H), 5.35 (d, J=17.2 Hz, 1H), 5.23 (d, J=10.3 Hz, 1H), 4.26 (s, 1H), 3.89 (s, 2H), 3.85 (t, J=4.8 Hz, 4H), 3.69 (t, J=4.7 Hz, 4H).

Example 7

Example 7.1: Preparation of 5-allyloxyquinoline

After adding sodium hydride (60% dispersion in mineral oil, 90 mg, 2.25 mmol) to a round-bottomed flask set to 0° C. using ice and water, DMF (17.4 mL) was slowly dropped. Then, 5-hydroxylquinoline (252 mg, 1.74 mmol) dissolved in DMF (4.0 mL) was slowly dropped to the round-bottomed flask. The temperature of the reaction mixture was raised to room temperature for 10 minutes. Ally bromide (0.165 mL, 1.91 mmol) was slowly dropped to the resulting yellow reaction mixture. After confirming the termination of reaction by TLC (ethyl acetate:hexane=1:4, $R_f$=0.5), H$_2$O was added to the reaction mixture. The reaction mixture was separated into an ethyl acetate layer and an H$_2$O layer using a separatory funnel. After drying the organic layer with anhydrous MgSO$_4$, the solvent was removed by vacuum distillation. The mixture was purified by silica gel column chromatography (ethyl acetate:hexane=1:4) to obtain the target compound (yellow oil, 296 mg, 92%).

$^1$H NMR (CDCl$_3$, 300 MHz) δ 8.90 (dd, J$_1$=4.2 Hz, J$_2$=1.7 Hz, 1H), 8.62 (dt, J$_1$=8.5 Hz, J$_2$=0.8 Hz, 1H), 7.70 (d, J=8.5 Hz, 1H), 7.59 (t, J=8.1 Hz, 1H), 7.37 (dd, J$_1$=8.5 Hz, J$_2$=4.2 Hz, 1H), 6.85 (d, J=7.7 Hz, 1H), 6.22-6.09 (m, 1H), 5.51 (dt, $J_1$=17.3 Hz, $J_2$=1.5 Hz, 1H), 5.35 (dq, $J_1$=10.5 Hz, $J_2$=1.3 Hz, 1H), 4.71 (dt, $J_1$=5.1 Hz, $J_2$=1.4 Hz, 2H).

Example 7.2: Preparation of 5-allyloxy-2-chloroquinoline

After dissolving 5-(allyloxy)quinoline (296 mg, 1.60 mmol) in dichloromethane (8.0 mL) and then adding mCPBA (406 mg, 1.34 mmol) at 0° C., the mixture was stirred at room temperature for 2 hours. After confirming the formation of N-oxide by TLC (ethyl acetate:hexane=1:4, $R_f$=0.1), $H_2O$ was slowly dropped. The reaction mixture was separated into a dichloromethane layer and an $H_2O$ layer using a separatory funnel. After drying the organic layer with anhydrous $MgSO_4$, the solvent was removed by vacuum distillation. After dissolving the dried N-oxide mixture in dichloromethane (8.0 mL), $POCl_3$ (0.22 mL, 2.36 mmol) was slowly added. The reaction mixture was stirred at 50° C. for 7 hours. After confirming the termination of reaction by TLC (ethyl acetate:hexane=1:4, $R_f$=0.7), $H_2O$ was slowly dropped. The reaction mixture was separated into a dichloromethane layer and an $H_2O$ layer using a separatory funnel. After drying the organic layer with anhydrous $MgSO_4$, the solvent was removed by vacuum distillation. The mixture was purified by silica gel column chromatography (ethyl acetate:hexane=1:4) to obtain the target compound (colorless oil, 138 mg, 39%).

$^1$H NMR (CDCl$_3$, 300 MHz) δ 8.56 (d, J=8.7 Hz, 1H), 7.61 (d, J=5.6 Hz, 1H), 7.61 (d, J=3.1 Hz, 1H), 7.36 (d, J=8.7 Hz, 1H), 6.88 (dd, $J_1$=5.6 Hz, $J_2$=3.1 Hz, 1H), 6.21-6.09 (m, 1H), 5.50 (dd, $J_1$=17.3 Hz, $J_2$=1.5 Hz, 1H), 5.37 (dd, $J_1$=10.5 Hz, $J_2$=1.3 Hz, 1H), 4.72 (dt, $J_1$=5.2 Hz, $J_2$=1.4 Hz, 2H).

Example 7.3: Preparation of 5-allyloxy-N-cyclopentylquinolin-2-amine (Compound 7)

After adding 5-(allyloxy)-2-chloroquinoline (16 mg, 72.8 μmol) to a vial, cyclopentylamine (108 μL, 1.09 mmol) was slowly added. The reaction mixture was stirred at 140° C. for 70 hours. After confirming the termination of reaction by TLC, $H_2O$ was slowly dropped. The reaction mixture was separated into an ethyl acetate layer and an $H_2O$ layer using a separatory funnel. After drying the organic layer with anhydrous $MgSO_4$, the solvent was removed by vacuum distillation. The mixture was purified by silica gel column chromatography (ethyl acetate:hexane=1:4) to obtain the target compound (colorless oil, 7 mg, 36%).

$^1$H NMR (CDCl$_3$, 300 MHz) δ 8.30 (d, J=9.1 Hz, 1H), 7.39 (t, J=8.1 Hz, 1H), 7.23 (d, J=8.5 Hz, 1H), 6.63 (d, J=9.1 Hz, 1H), 6.56 (d, J=7.7 Hz, 1H), 6.18-6.09 (m, 1H), 5.47 (dd, $J_1$=17.3 Hz, $J_2$=1.6 Hz, 1H), 5.31 (dd, $J_1$=10.5 Hz, $J_2$=1.4 Hz, 1H), 4.95 (bs, 1H), 4.66 (dd, $J_1$=3.7 Hz, $J_2$=1.4 Hz, 2H), 4.28-4.19 (m, 1H), 2.15-2.07 (m, 2H), 1.78-1.71 (m, 4H), 1.56-1.49 (m, 2H).

Example 8: Preparation of 5-allyloxy-2-(pyrrolidin-1-yl)quinoline (Compound 8)

Compound 8 having a pyrrolidine substituent was obtained in the same manner as in Example 7.3.

$^1$H NMR (CDCl$_3$, 400 MHz) δ 8.30 (d, J=9.2 Hz, 1H), 7.39 (t, J=8.1 Hz, 1H), 7.31 (d, J=8.4 Hz, 1H), 6.67 (d, J=9.2 Hz, 1H), 6.54 (d, J=7.6 Hz, 1H), 6.20-6.10 (m, 1H), 5.49 (dd, $J_1$=17.3 Hz, $J_2$=1.6 Hz, 1H), 5.32 (dd, $J_1$=10.5 Hz, $J_2$=1.4 Hz, 1H), 4.66 (dd, $J_1$=5.1 Hz, $J_2$=1.4 Hz, 2H), 3.63-3.60 (m, 4H), 2.03-2.00 (m, 4H).

Example 9: Preparation of 5-allyloxy-2-(piperidin-1-yl)quinoline (Compound 9)

Compound 9 having a piperidine substituent was obtained in the same manner as in Example 7.3.

$^1$H NMR (CDCl$_3$, 300 MHz) δ 8.30 (d, J=9.3 Hz, 1H), 7.39 (t, J=8.1 Hz, 1H), 7.27 (d, J=9.5 Hz, 1H), 6.94 (d, J=9.4 Hz, 1H), 6.56 (d, J=7.7 Hz, 1H), 6.21-6.08 (m, 1H), 5.48 (dd, $J_1$=17.3 Hz, $J_2$=1.6 Hz, 1H), 5.32 (d, J=11.6 Hz, 1H), 4.66 (dd, $J_1$=5.1 Hz, $J_2$=1.3 Hz, 2H), 3.73-3.71 (m, 4H), 1.68 (bs, 6H).

Example 10: Preparation of 4-(5-allyloxyquinoline-2-yl)morpholine (Compound 10)

Compound 10 having a morpholino substituent was obtained in the same manner as in Example 7.3.

$^1$H NMR (CDCl$_3$, 400 MHz) δ 8.37 (d, J=9.3 Hz, 1H), 7.43 (t, J=8.1 Hz, 1H), 7.32 (d, J=8.5 Hz, 1H), 6.90 (d, J=9.3 Hz, 1H), 6.61 (d, J=7.7 Hz, 1H), 6.20-6.10 (m, 1H), 5.49 (dt, $J_1$=17.3 Hz, $J_2$=1.5 Hz, 1H), 5.33 (dt, $J_1$=10.5 Hz, $J_2$=1.3 Hz, 1H), 4.67 (dd, $J_1$=5.1 Hz, $J_2$=1.4 Hz, 2H), 3.84 (t, J=4.8 Hz, 4H), 3.70 (t, J=7.8 Hz, 4H).

Example 11: Preparation of 5-allyloxy-N-phenylquinolin-2-amine (Compound 11)

Compound 11 having an aniline substituent was obtained in the same manner as in Example 7.3.

$^1$H NMR (CDCl$_3$, 400 MHz) δ 8.39 (d, J=9.1 Hz, 1H), 7.55 (d, J=7.9 Hz, 2H), 7.47 (t, J=8.1 Hz, 1H), 7.32 (d, J=8.5 Hz, 3H), 7.09 (t, J=7.3 Hz, 1H), 6.96 (d, J=9.0 Hz, 2H), 6.66 (d, J=7.7 Hz, 1H), 6.20-6.10 (m, 1H), 5.50 (d, J=17.2 Hz, 1H), 5.34 (d, J=10.5 Hz, 1H), 4.69 (dd, $J_1$=3.3 Hz, $J_2$=1.7 Hz, 2H).

Example 12: Preparation of 2-cyclopentylaminoquinolin-5-ol (Compound 12)

After adding 5-(allyloxy)-N-cyclopentylquinolin-2-amine (15 mg, 55.9 μmol) to a vial and adding methanol (0.57 mL), the mixture was stirred while purging with $N_2$ (g). 10 minutes later, after adding Pd(PPh$_3$)$_4$ (655 μg, 0.567 μmol), the mixture was stirred. 5 minutes later, $K_2CO_3$ (24 mg, 174 μmol) was added. The resulting yellow reaction mixture was stirred at room temperature for 10 hours while purging with $N_2$ (g). After confirming the termination of reaction by TLC (ethyl acetate:hexane=1:1, $R_f$=0.5), the reaction mixture was filtered with methanol using a glass filter. The solvent was removed from the filtrate by vacuum distillation. The mixture was purified by silica gel column chromatography (ethyl acetate:hexane=1:1) to obtain the target compound (yellow solid, 10 mg, 78%).

$^1$H NMR (CD$_3$OD, 300 MHz) δ 8.17 (d, J=9.1 Hz, 1H), 7.28 (t, J=8.0 Hz, 1H), 7.10 (d, J=8.4 Hz, 1H), 6.67 (d, J=9.2 Hz, 1H), 6.55 (d, J=7.6 Hz, 1H), 4.34 (quintet, J=6.3 Hz, 1H), 2.12-2.02 (m, 2H), 1.79-1.64 (m, 4H), 1.30-1.52 (m, 2H).

Example 13: Preparation of 2-(pyrrolidin-1-yl)quinolin-5-ol (Compound 13)

Compound 13 having a pyrrolidine substituent was obtained in the same manner as in Example 12.

¹H NMR (CD₃OD, 300 MHz) δ 8.27 (d, J=9.3 Hz, 1H), 7.28 (t, J=8.1 Hz, 1H), 7.15 (d, J=8.4 Hz, 1H), 6.76 (d, J=9.2 Hz, 1H), 6.53 (d, J=7.6 Hz, 1H), 3.61-3.57 (m, 4H), 2.07-2.01 (m, 4H).

Example 14: Preparation of
2-(piperidin-1-yl)quinolin-5-ol (Compound 14)

Compound 14 having a piperidine substituent was obtained in the same manner as in Example 12.
¹H NMR (CDCl₃, 300 MHz) δ 8.24 (d, J=9.4 Hz, 1H), 7.32 (t, J=7.5 Hz, 1H), 7.31 (d, J=6.6 Hz, 1H), 6.97 (d, J=9.4 Hz, 1H), 6.52 (dd, J₁=6.6 Hz, J₂=1.7 Hz, 1H), 3.74 (m, 4H), 1.69 (m, 6H).

Example 15: Preparation of
2-(phenylamino)quinolin-5-ol (Compound 15)

Compound 15 having an aniline substituent was obtained in the same manner as in Example 12.
¹H NMR (CDCl₃, 300 MHz) δ 8.39 (d, J=9.1 Hz, 1H), 7.46 (d, J=8.6 Hz, 2H), 7.39-7.34 (m, 4H), 7.11 (t, J=7.3 Hz, 1H), 7.02 (d, J=9.1 Hz, 1H), 6.68 (dd, J₁=5.5 Hz, J₂=3.0 Hz, 1H).

Example 16: Preparation of
2-morpholinoquinolin-5-ol (Compound 16)

Compound 16 having a morpholino substituent was obtained in the same manner as in Example 12.
¹H NMR (CDCl₃, 300 MHz) δ 8.31 (d, J=9.3 Hz, 1H), 7.35-7.30 (m, 2H), 6.94 (d, J=9.3 Hz, 1H), 6.56 (d, J=6.9 Hz, 1H), 3.87-3.84 (m, 4H), 3.74-3.71 (m, 4H).

Example 17

Example 17.1: Preparation of
5-propargyloxyquinoline

After adding sodium hydride (60% dispersion in mineral oil, 16 mg, 393 μmol) to a round-bottomed flask at 0° C., DMF (1.0 mL) was slowly dropped. 5-Hydroxylquinoline (43.9 mg, 0.302 mmol) dissolved in DMF (2.0 mL) was slowly dropped to the round-bottomed flask. 10 minutes later, after slowly dropping propargyl bromide (80% in toluene, 37.1 μmL, 333 μmol) to the resulting yellow reaction mixture, the temperature of the reaction mixture was raised to room temperature. After confirming the termination of reaction by TLC (ethyl acetate:hexane=1:4, R_f=0.3), H₂O was added to the reaction mixture. The reaction mixture was separated into an ethyl acetate layer and an H₂O layer using a separatory funnel. After drying the organic layer with anhydrous MgSO₄, the solvent was removed by vacuum distillation. The mixture was purified by silica gel column chromatography (ethyl acetate:hexane=1:4) to obtain the target compound (white solid, 52 mg, 94%).
¹H NMR (CDCl₃, 300 MHz) δ 8.91 (dd, J₁=4.2 Hz, J₂=1.7 Hz, 1H), 8.59 (dt, J₁=8.5 Hz, J₂=0.8 Hz, 1H), 7.74 (d, J=8.6 Hz, 1H), 7.62 (t, J=8.1 Hz, 1H), 7.39 (dd, J₁=8.5 Hz, J₂=4.2 Hz, 1H), 7.00 (d, J=7.7 Hz, 1H), 4.90 (d, J=2.4 Hz, 2H), 2.56 (t, J=2.4 Hz, 1H).

Example 17.2: Preparation of
2-chloro-5-propargyloxyquinoline

After dissolving 5-propazyloxyquinoline (52 mg, 2.84 μmol) in dichloromethane (1.42 mL) and adding mCPBA (94.3 mg, 31.1 μmol) at 0° C., the mixture was stirred at room temperature for 2.5 hours. After confirming the formation of N-oxide by TLC (ethyl acetate:hexane=1:1, R_f=0.1), H₂O was slowly dropped. Then, 4 N NaOH was slowly added until the pH reached 14. The reaction mixture was separated into a dichloromethane layer and an H₂O layer using a separatory funnel. After drying the organic layer with anhydrous MgSO₄, the solvent was removed by vacuum distillation. After dissolving the dried N-oxide mixture in dichloromethane (1.42 mL), POCl₃ (39.6 μL, 42.5 μmol) was slowly added. The reaction mixture was stirred at 50° C. for 5.5 hours. After confirming the termination of reaction by TLC (ethyl acetate:hexane=1:40, R_f=0.7), H₂O was slowly dropped. The reaction mixture was separated into a dichloromethane layer and an H₂O layer using a separatory funnel. After drying the organic layer with anhydrous MgSO₄, the solvent was removed by vacuum distillation. The mixture was purified by silica gel column chromatography (ethyl acetate:hexane=1:40) to obtain the target compound (white solid, 25 mg, 40%).
¹H NMR (CDCl₃, 300 MHz) δ 8.53 (d, J=8.8 Hz, 1H), 7.65 (s, 1H), 7.64 (d, J=1.3 Hz, 1H), 7.37 (d, J=8.8 Hz, 1H), 7.01 (t, J=4.3 Hz, 1H), 4.90 (d, J=2.4 Hz, 2H), 2.57 (t, J=2.4 Hz, 1H).

Example 17.3: Preparation of
5-propargyloxy-2-(pyrrolidin-1-yl)quinoline
(Compound 17)

After adding 2-chloro-5-(propargyloxy)quinoline (25 mg, 115 μmol) to a vial, pyrrolidine (143 μL, 1.71 mmol) was slowly added. The reaction mixture was stirred at 80° C. for 2 hours. After confirming the termination of reaction by TLC (ethyl acetate:hexane=1:4, R_f=0.7), H₂O was slowly dropped. The reaction mixture was separated into an ethyl acetate layer and an H₂O layer using a separatory funnel. After drying the organic layer with anhydrous MgSO₄, the solvent was removed by vacuum distillation. The mixture was purified by silica gel column chromatography (ethyl acetate:hexane=1:1) to obtain the target compound (white solid, 15 mg, 52%).
¹H NMR (CDCl₃, 400 MHz) δ 8.26 (d, J=9.2 Hz, 1H), 7.41 (t, J=8.1 Hz, 1H), 7.34 (d, J=8.4 Hz, 1H), 6.67 (d, J=9.3 Hz, 1H), 6.65 (d, J=7.7 Hz, 1H), 4.83 (d, J=2.4 Hz, 2H), 3.62-3.61 (m, 4H), 2.55 (t, J=2.4 Hz, 1H), 2.04-2.01 (m, 4H).

Test Example 1: Experiment with Tet-Inducible ESET/SETDB1 Cell Line

In order to find compounds that inhibit the ESET/SETDB1 enzyme, 107 compounds expected to inhibit the activity of ESET/SETDB1 were selected through structural modeling from a compound library. These compounds were screened using a Tet-inducible ESET cell line.

Tet-Inducible ESET (H3K9 Specific Histone Methyltransferase) Cell Line (Tetracycline-Inducible ESET Cells):
A Tet-inducible ESET cell line was prepared using the T-REx™ system available from Invitrogen. The myc-ESET gene was subcloned into pcDNA5/TO and transfected into somatic mother cells (STHdh$^{Q7/7}$, striatal cells) using pcDNA6/TR. After treating with doxycyline (4 μg/mL), the cell line that exhibit increase in ESET was used in the following experiment.

Confocal Microscopy for Determination of H3K9me3 (Confocal Microscopy for Identification of Change in Heterochromatin Condensation by H3K9Me3 and Drug)

An indirect fluorescence labeling method using fluorescein-conjugated secondary antibodies was used. After fixing ESET inducible cells with 4% PFA and incubating with H3K9me3 (rabbit antibody; dilution, 1:200; Millipore) primary antibodies, the cells were incubated with fluorescence-conjugated secondary antibodies (Alexa 594; dilution, 1:400; Thermo). Images were obtained using a confocal microscope (IX2-DSU, Olympus, Tokyo, Japan).

Figure 1:
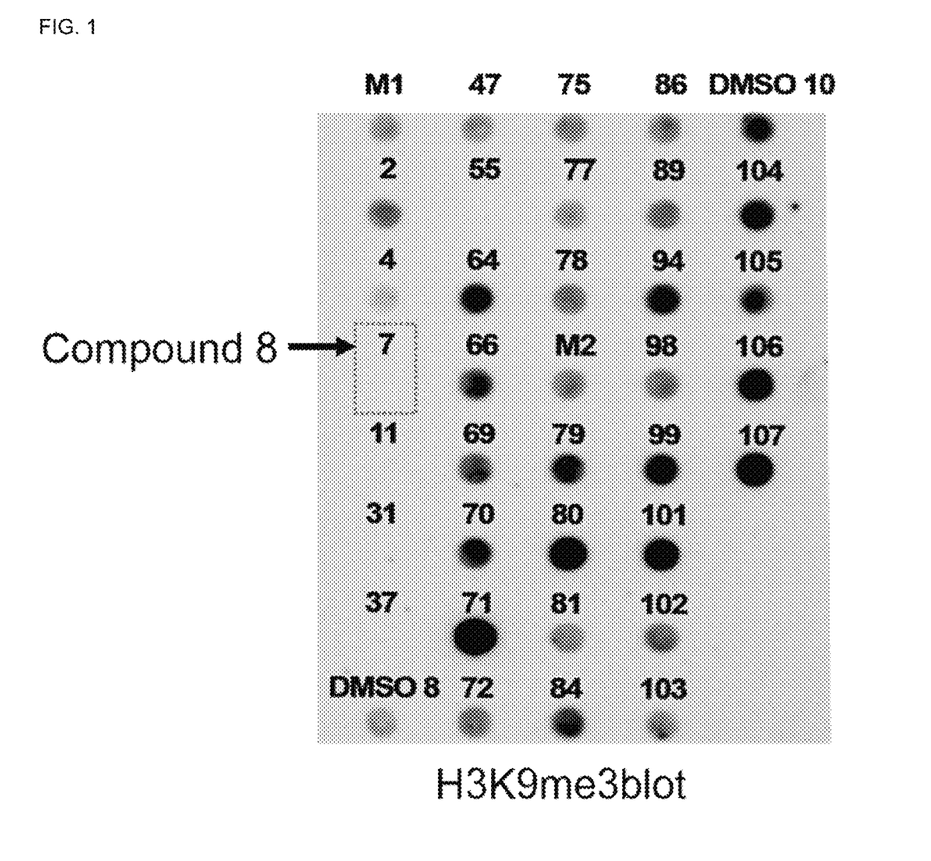
FIG. 1 shows experimental results for compounds prepared according to an exemplary embodiment of the present disclosure for a Tet-inducible ESET/SETDB1 cell line.

From dot blot analysis, compounds 4, 7, 11, 31 and 55 were confirmed to show significant inhibitory effect against ESET/SETDB1 among the selected 107 compounds, as shown in FIG. 1. Among those compounds, #7 compound was a quinolone derivative, which is selected as a hit-compound through the instant experiment. The #7 compound in FIG. 1 is Compound 8 in the present invention.

Test Example 2: ESET/SETDB1 Enzyme Assay

In order to investigate the inhibitory effect against the activity of the ESET/SETDB1 enzyme of the compounds according to the present disclosure, SETDB1 chemiluminescence assay was conducted for the compound 8. The SETDB1 assay was performed using the SetDB1 chemiluminescent assay kit (BPS Bioscience) according to the manufacturer's protocol. S-Adenosylmethionine (SAM, stock concentration 20 µM) was used as a positive control compound. First, SAM and the test compounds were prepared to final concentrations of 1 µM, 3 µM, 10 µM, 30 µM and 100 µM by diluting with DMSO (final volume 1 µL). 150 µL of a TBST buffer (1×TBS, pH 8.0, containing 0.05% Tween-20) was added to each well of a 96-well plate and hydrated at room temperature for 15 minutes. A master mix containing an assay buffer, the compound 8 and the SETDB1 enzyme was prepared.

25 µL (7.5 µL 4×HMT buffer+2.5 µL 20 µM SAM+15 µL H$_2$O) of the prepared master mix was added to each well of the plate. Then, 1 µL of the test compound (1 µM, 3 µM, 10 µM, 30 µM or 100 µM) and 20 µL of the diluted SetDB1 enzyme were added sequentially. As a negative control, 1 µL of an inhibitor buffer and 20 µL of a 1×HMT assay buffer were added. After incubation at room temperature for 1 hour and 30 minutes, an assay was performed using an antibody that recognizes the methylated K9 residue of histone H3 and a HRP-conjugated secondary antibody. Chemiluminescence resulting from the reaction between the HRP-conjugated secondary antibody and the added HRP substrate was measured using a chemiluminescence reader (Molecular Devices microplate reader) and the result was analyzed using the SoftMax Pro software.

Figure 2:
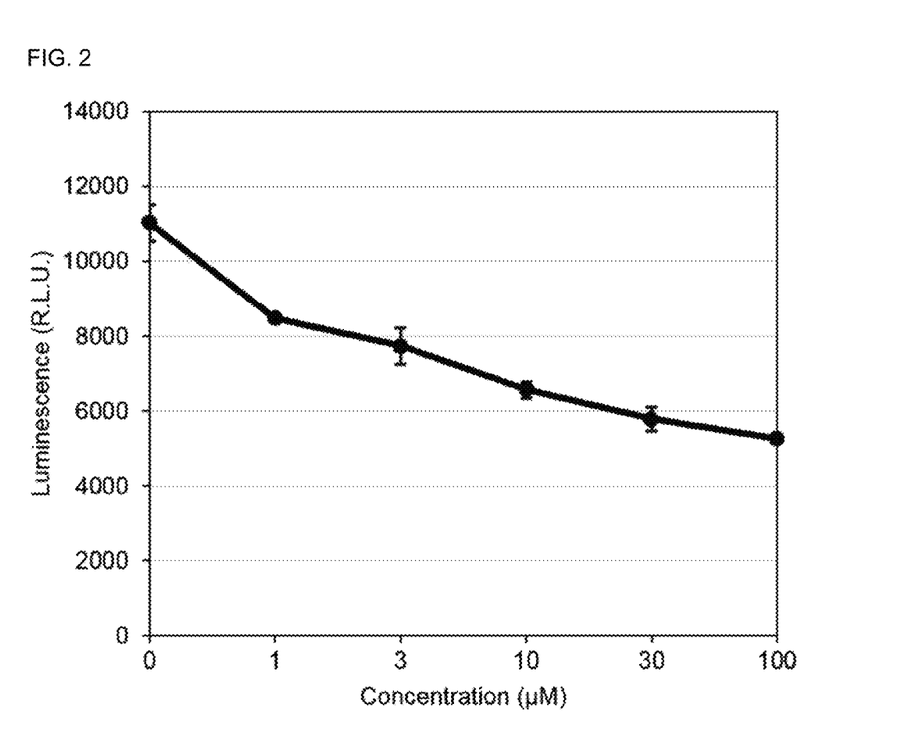
FIG. 2 is a graph showing ESET/SETDB1 enzyme assays result for a compound prepared according to an exemplary embodiment of the present disclosure.

FIG. 2 shows the result of the chemiluminescence assay. It can be seen that the compound 8 according to the present disclosure show remarkably decreased trimethylation of H3K9 (H3K9me3).

Test Example 3: Rotarod Performance Test in YAC128 Animal Model

The effect of the compound according to the present disclosure on motor ability was evaluated using the transgenic YAC128 mouse which expresses the human Huntingtin gene containing 128 CAG repeat sequences as a model of Huntington's disease (HD) (Menalled L et al., 2009, Neurobiol Dis 35(3):319-36). The Huntington's disease model mouse is reported to show decline in motor ability, which is the typical pathological symptom of Huntington's disease, from 6 around months after birth, progress of neurodegeneration from 9 months and aggregation of mutant Huntington's genes in striatal neurons from around 18 months.

Rotarod performance test was conducted using 15-month-old male YAC128 mice. The drug was administered (0.636 mg/kg) for 3 weeks, 5 days a week, and the rotarod test was performed on the 5th day of each week.

The mouse was placed on a rotating rod (4 cm in diameter) and riding time was measured. The experiment was performed 4 times on the same day and 60 seconds was given to each mouse. The rotarod rotation speed was set to 5 rpm. The period of time until the mouse fell to the ground was measured. When the mouse remained longer than 60 seconds on the rod, the riding time was recorded as 60 seconds. The recorded time was statistically analyzed and was used as an indicator of the motor ability and balance of the mouse.

Figure 3:
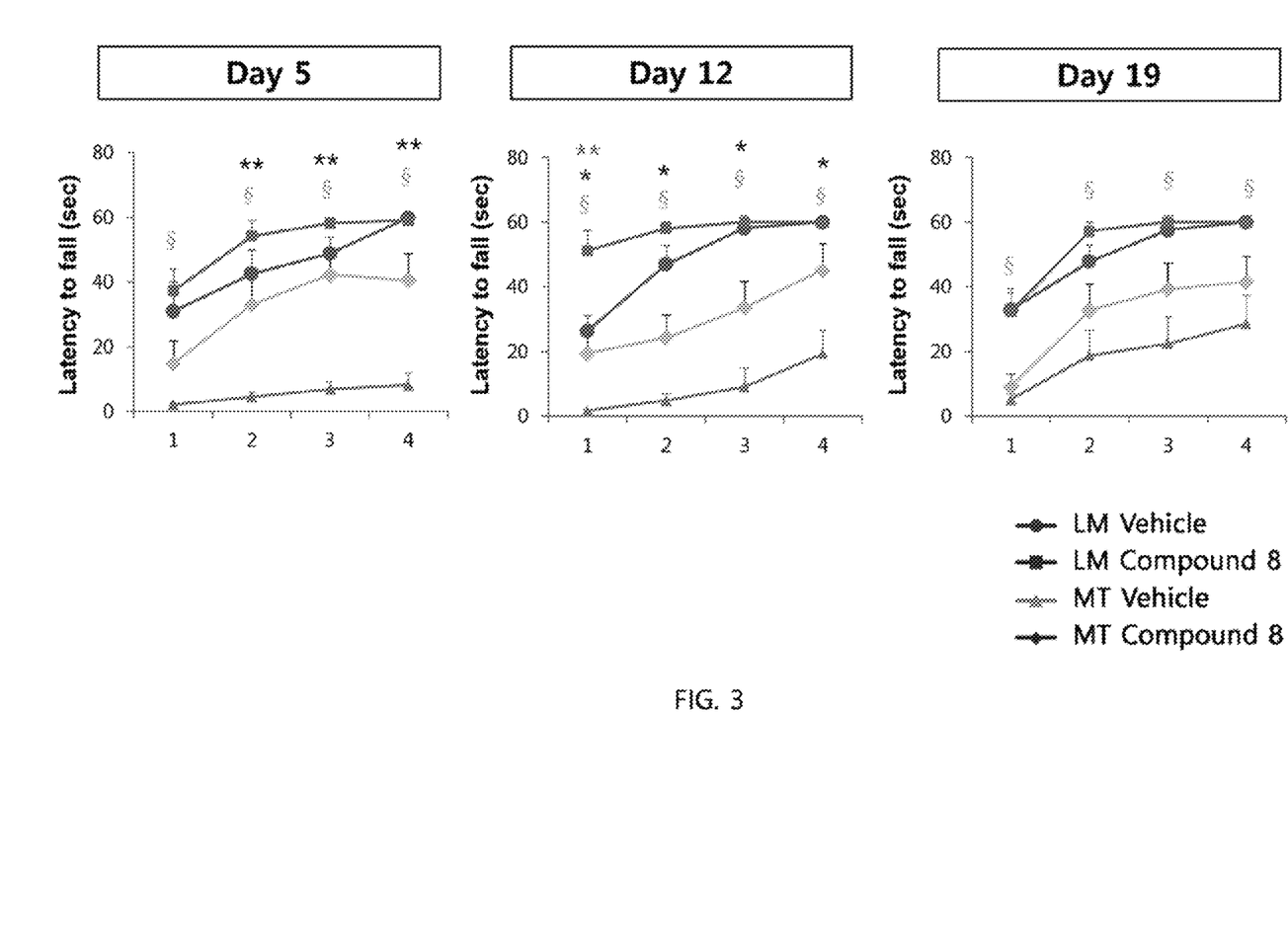
FIG. 3 shows a rotarod performance test for a compound prepared according to an exemplary embodiment of the present disclosure in a YAC128 animal model.

As seen from FIG. 3, the mouse treated with the compound 8 according to the present disclosure showed remarkably increased riding time on the rod as compared to the vehicle and the difference was more noticeable as the rotarod performance test was repeated. The riding time in the rotarod performance test was short at first but was increased as the test was repeated, probably due to the learning effect.

Test Example 4: Measurement of Change in H3K9 Trimethylation in Brain of YAC128 Mouse after Administration of Compound According to the Present Disclosure

After adding the striatal brain tissue of YAC128 mouse to 1 mL of PBS containing 0.4 mM sodium butyrate, 5% Triton X-100, 3 mM DTT, 1 mM sodium orthovanadate, 5 mM sodium fluoride, 3 mM PMSF, 0.5 mg/mL leupeptin and 10 mg/mL aprotinin, a cell homogenate was obtained using a Downce crusher. After centrifugation at 3000 rpm for 10 minutes, the supernatant was removed. The precipitating cell pellet was washed twice with a 5% Triton buffer and histone was extracted with 0.2 M HCl. After neutralizing the histone-containing solution to neutral pH with 1 N NaOH, proteins were quantitated and separated by 15% SDS-PAGE. The change in trimethylation of H3K9 (H3K9me3) was investigated using anti-H3K9me3 (rabbit antibody; dilution, 1:1000; Millipore).

Figure 4A:
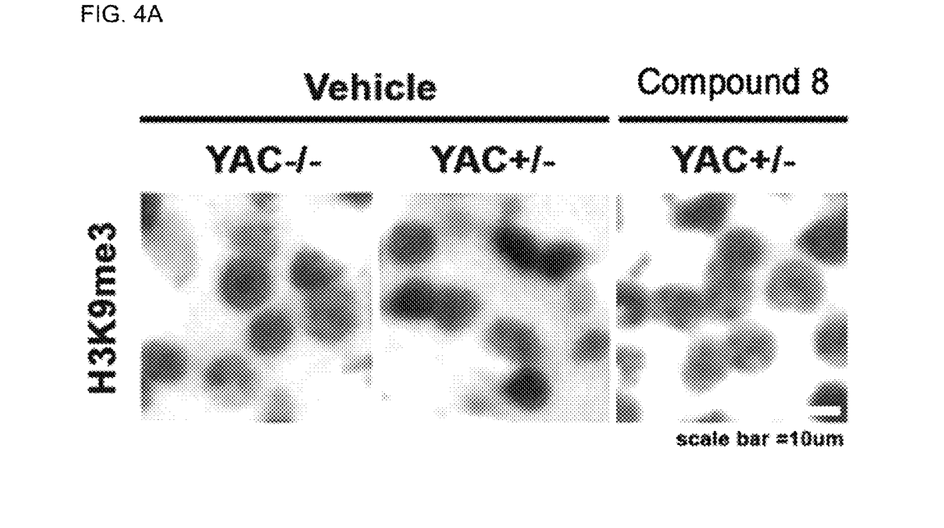
FIGS. 4A and 4B show a result of measuring the effect of a compound prepared according to an exemplary embodiment of the present disclosure on change of H3K9 trimethylation in the brain in a YAC128 animal model.
Figure 4B:
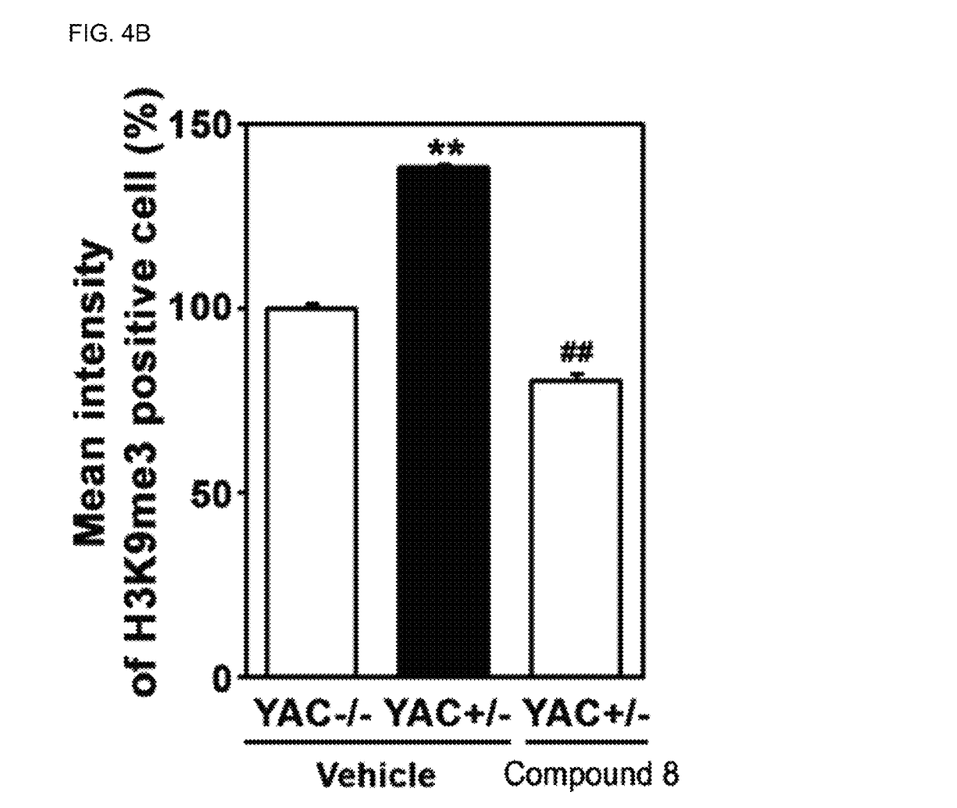

As seen from FIGS. 4A and 4B, It can be seen that the group treated with the compound 8 according to the present disclosure showed remarkably decreased intensity of trimethylated H3K9.

What is claimed is:

1. A quinoline derivative represented by [Chemical Formula 1] or a pharmaceutically acceptable salt thereof, which inhibits histone methyltransferase (H3K9 methyltransferase):

[Chemical Formula 1]

wherein

Z is O or NH, each of $R_1$ and $R_2$, which are identical to or different from each other, is independently selected from H, $C_{1-6}$ alkyl, hydroxy $C_{1-6}$ alkyl, phenyl and $C_{4-7}$ cycloalkyl, wherein the phenyl is unsubstituted or substituted with a substituent selected from OH, $NO_2$, $C_{1-3}$ alkyl, $C_{1-3}$ alkoxy and trifluoromethyl, the $R_2$ is $C_{4-7}$ cycloalkyl if the $R_1$ is H, the $R_1$ is $C_{4-7}$ cycloalkyl if the $R_2$ is H, and the $R_1$ and the $R_2$ may be linked with each other to form a ring if they are $C_{1-6}$ alkyl or hydroxy $C_{1-6}$ alkyl, and $R_3$ is selected from $C_{1-10}$ alkyl, vinyl, allyl $C_{0-6}$ alkyl and propargyl $C_{0-6}$ alkyl.

2. The quinoline derivative or the pharmaceutically acceptable salt thereof according to claim 1, wherein the histone methyltransferase is ESET (erythroblast transformation specific-related gene associated protein with SET domain) which induces methylation of histone H3 lysine 9.

3. The quinoline derivative or the pharmaceutically acceptable salt thereof according to claim 1, wherein the histone methyltransferase is SETDB1 (SET domain, bifurcated 1) which induces methylation of histone H3 lysine 9.

4. The quinoline derivative or the pharmaceutically acceptable salt thereof according to claim 1, wherein the quinoline compound represented by [Chemical Formula 1] is selected from the compounds represented by [Chemical Formula 2] through [Chemical Formula 4]:

[Chemical Formula 2]

[Chemical Formula 3]

[Chemical Formula 3]

wherein

Z is O or NH,

Y is C or O, $R_3$ is selected from $C_{1-10}$ alkyl, vinyl, allyl $C_{0-6}$ alkyl and propargyl $C_{0-6}$ alkyl, $R_4$ is selected from H, OH, $NO_2$, a halogen, $C_{1-3}$ alkyl, $C_{1-3}$ alkoxy and trifluoromethyl, and each of n and m, which are identical to or different from each other, is independently an integer from 1 to 5.

5. The quinoline derivative or the pharmaceutically acceptable salt thereof according to claim 1, wherein the quinoline compound is selected from Compound 1 through 14 and Compound 16 through Compound 17:

Compound 1: $N^2$-cyclopentyl-$N^5$-allylquinoline-2,5-diamine;

Compound 2: $N^2$-cyclohexyl-$N^5$-allylquinoline-2,5-diamine;

Compound 3: 2-(pyrrolidin-1-yl)-N-allylquinolin-5-amine;

Compound 4: 2-(piperidin-1-yl)-N-allylquinolin-5-amine;

Compound 5: $N^2$-phenyl-$N^5$-allylquinoline-2,5-diamine;

Compound 6: 2-morpholino-N-allylquinolin-5-amine;

Compound 7: 5-allyloxy-N-cyclopentylquinolin-2-amine;

Compound 8: 5-allyloxy-2-(pyrrolidin-1-yl)quinoline;

Compound 9: 5-allyloxy-2-(piperidin-1-yl)quinoline;

Compound 10: 4-(5-allyloxyquinoline-2-yl)morpholine;

Compound 11: 5-allyloxy-N-phenylquinolin-2-amine;

Compound 12: 2-cyclopentylaminoquinolin-5-ol;

Compound 13: 2-(pyrrolidin-1-yl)quinolin-5-ol;

Compound 14: 2-(piperidin-1-yl)quinolin-5-ol;

Compound 16: 2-morpholinoquinolin-5-ol; and

Compound 17: 5-propargyloxy-2-(pyrrolidin-1-yl)quinoline.

6. The quinoline derivative or the pharmaceutically acceptable salt thereof according to claim 1, wherein the pharmaceutically acceptable salt is selected from hydrochloride, bromate, sulfonate, amidosulfate, phosphate, nitrate, acetate, propionate, succinate, glycolate, stearate, lactate, tartrate, citrate, p-toluenesulfonate and methanesulfonate.

* * * * *